United States Patent [19]

Hughes et al.

[11] Patent Number: 4,728,328
[45] Date of Patent: Mar. 1, 1988

[54] CUFFED TUBULAR ORGANIC PROSTHESES

[75] Inventors: Howard C. Hughes, Cornwall; Jacob T. Kissinger, Mechanicsburg, both of Pa.

[73] Assignee: Research Corporation, New York, N.Y.

[21] Appl. No.: 740,358

[22] Filed: Jun. 3, 1985

Related U.S. Application Data

[63] Continuation-in-part of Ser. No. 663,008, Oct. 19, 1984, abandoned.

[51] Int. Cl.$^4$ .............................................. A61F 2/04
[52] U.S. Cl. ............................................ 623/12; 623/1; 128/334 R
[58] Field of Search ..................... 623/1, 12, 11, 66; 128/334 R

[56] References Cited

U.S. PATENT DOCUMENTS

| 3,783,454 | 1/1974 | Sausse et al. | 623/12 |
| 4,182,339 | 1/1980 | Hardy, Jr. | 623/1 X |
| 4,485,227 | 11/1984 | Fox | 623/1 X |

FOREIGN PATENT DOCUMENTS 2139897 11/1984 United Kingdom ..................... 623/1

Primary Examiner—Richard J. Apley
Assistant Examiner—Alan W. Cannon
Attorney, Agent, or Firm—Scully, Scott, Murphy & Presser

[57] ABSTRACT

A cuffed tubular vascular prosthesis and process for manufacturing the prosthesis are disclosed. A flexible tubular body is formed by coating a glass rod with a polymer solution and air-curing the coating to form a smooth outer surface. The tubular body is removed from the glass rod and turned inside out so that the smooth air cured surface forms the inner wall of the prosthesis. Prosthesis cuffs are formed on the distal ends of the prosthesis by folding the edges of the tubular body back over itself and bonding the turned back edges to the body. The prosthesis is heat set to maintain the cuffs in position during anastomosis. A double cuffed prosthesis is provided by sliding a suture sleeve over the prosthesis cuff, folding the sleeve back over itself and bonding to the prosthesis cuff and the tubular body. The prostheses provide an air-cured non thrombogenetic inner surface to prevent occlusion and efficient separation of the sutures from the lumen of the vessel or tubular organ being repaired to prevent tissue reactivity and thrombosis.

26 Claims, 12 Drawing Figures

CUFFED TUBULAR ORGANIC PROSTHESES

CROSS REFERENCE TO RELATED APPLICATION

This application is a continuation-in-part application of the Applicants' pending U.S. patent application Ser. No. 663,008, filed Oct. 19, 1984, entitled "Cuffed Vascular Prostheses", now abandoned.

BACKGROUND OF THE INVENTION

1. Field of the Invention

The present invention relates to tubular organic prostheses for permanent implantation within the body and the method for manufacturing the prostheses.

2. Description of the Prior Art

Tubular prostheses have been used for many years for the repair and replacement of hollow tubular organs. Vascular prostheses have been used to accomplish by-pass operations and to repair damaged vessels in the body such as veins. Often, a piece of one's own vessel is taken from another part of the body to form the prosthesis. This involves putting the patient through an additional surgical procedure. In addition, in many patients, suitable vessels are not available.

Synthetic grafts were developed to overcome the above problems with the natural grafts. The grafts are made of woven fabric such as those illustrated in U.S. patent application Nos. 3,620,218 and 3,463,158 both issued to Schmitt, et al. The prior art fabric grafts encourage the initiation of tissue growth that partially blocks the grafts. In addition, at the ends of the grafts which are anastomosed to the recipient vessel, thrombosis may occur occluding the prosthesis. For these reasons, the prior art synthetic grafts are limited to diameters of 6 mm or larger. However, many patients require grafts for vessels smaller than 6 mm.

In U.S. Pat. No. 4,086,665 issued to Poirier, there is disclosed an artificial blood conduit consisting of a fabric tube surrounded by convolutions made of a silicon elastomer. Separate end connectors are provided for connecting to the vessels and organs. This conduit is for artificial hearts and blood pumps and is not well-suited for small vessel grafts of less than 6 mm in diameter.

Research in the manufacture of synthetic small blood vessel grafts is disclosed in an article entitled "A Sanguine Future for Biomaterials" in *Science Magazine*, Volume 217, Sept. 17, 1982. The article teaches surface coating of albumin on the conduit to reduce thrombogenicity. The article discloses conduits manufactured with long segments of polyether polyurethane which have a relatively high selectivity for the albumin. However, the use of albumin on the outer surface of the conduit will not reduce the thrombogenicity of the inner surface of the conduit that is in contact with the blood.

Furthermore, the connection between the prosthetic device and the tubular organ can cause problems. The ends of the tubular prostheses are generally sharp and may damage the live organ. U.S. Pat. No. 3,818,515 issued to Neville, discloses a bifurcated trachea prosthesis wherein the ends are tapered to facilitate entry into the appropriate vessel. One or more sleeves surround the ends of the device and are attached in a tongue and groove arrangement for suturing the device to the trachea. The sharp ends of the device may encourage infection and granulation tissue formation.

A method of connecting the ends of two tubular organs wherein one vessel is turned back over a connection device and the other vessel is pulled up over the turned back vessel, is disclosed in U.S. Pat. No. 3,774,615 issued to Lim et al. No means for suturing the vessels is disclosed.

Thus, there is a need for a synthetic tubular organic prosthesis having an inner surface and end connectors that will minimize neointimal hyperplasia, prevent thrombosis and permit the permanent implantation of the prosthesis in small blood vessels and other tubular organs.

SUMMARY OF THE INVENTION

In accordance with the present invention there is provided a cuffed tubular prosthesis to be permanently implanted within a body for repairing or replacing tubular organs. The prosthesis includes a flexible tubular body having a pair of prosthesis cuffs on each end of the tubular body. Each of the prosthesis cuffs have a smooth, rounded end that is integral with the tubular body and a free end that is bonded to the tubular body. The prosthesis is formed by coating a mandrel with a polymer solution and air-curing the coating thereby forming a smooth outer surface. The prosthesis is removed from the mandrel and is then turned inside out so that the air cured smooth surface forms the inner wall of the prosthesis. The prosthesis cuffs are formed by folding back the edges of the prosthesis over itself so that the ends of the prosthesis are rounded. The turned-back edges of the prosthesis are bonded to the tubular body.

When the prosthesis is anastomosed the sutures will pass through the prosthesis cuff and the endothelial surface of the vessel or organ to be repaired pulling the vessel up and over the prosthesis cuff. Thus, by attaching the prosthesis to the tubular organ away from the cut end, infection and granulation tissue formation will be minimized at the anastomosis, and long term stability of the prosthesis will be maximized.

Furthermore, when used to repair blood vessels the sutures are separated from the blood passing through the vessel thereby preventing thrombosis. Moreover, turning the prosthesis inside out so that the smooth air-cured surface contacts the endothelial surface of the vessel, has produced the unexpected result of minimizing thrombosis and neointimal hyperplasia. Thus, the nonthrombogenetic air-cured inner wall permits the prosthesis to be manufactured in sizes of 6 mm. or less which will not become occluded after extended use.

Suture cuffs that are bonded to the prosthesis cuffs and the tubular body may also be provided on both ends of the prosthesis. In this embodiment, the sutures will pass through the suture cuffs and the endothelial surface of the vessel to be repaired thereby further separating the sutures from the blood and preventing thrombosis.

The prosthesis of the present invention is well suited for the repair or replacement of vessels and other tubular organs such as the trachea, urethra, ureter, fallopian tubes, vas or ductus deferens and the esophagus. An embodiment especially useful as a trachea prosthesis includes a tubular body wrapped spirally with support coils bonded to the body. The support coils are coated with the same polymer coating used to form the body.

BRIEF DESCRIPTION OF THE DRAWINGS

The following is a detailed description together with accompanying drawings of an illustrative embodiment of the invention. It is to be understood that the inven

DETAILED DESCRIPTION OF THE INVENTION

Figure 1:
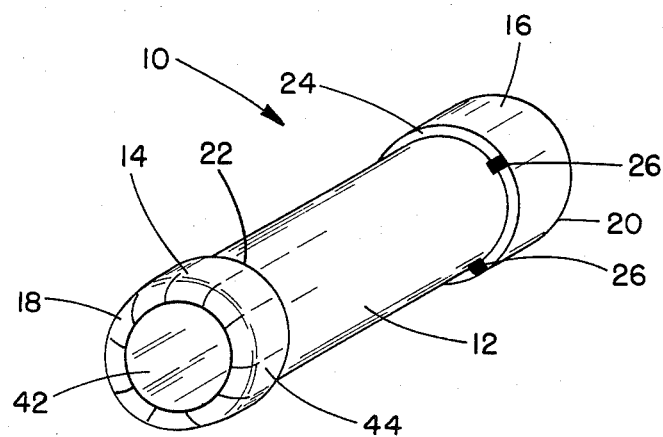
- FIG. 1 is a prospective view of the cuffed vascular prosthesis of the present invention.

In accordance with the present invention, there is provided a prosthesis generally indicated by the numeral 10 in FIG. 1. The prosthesis 10 includes a flexible tubular body 12 and a pair of prosthesis cuffs 14 and 16 on the distal ends of the tubular body 12. The prosthesis cuffs 14 and 16 are integral with the tubular body 12 and have smooth, rounded ends 18 and 20 that are inserted within the tubular organ being repaired. The free ends, 22 and 24, are bonded to the tubular body 12 by bonds 26 which may be placed at 60°-90° intervals around the circumference of the tubular body 12.

The prosthesis 10 of the present invention is made of a polymer material such as segmented polyether polyurethane. The process for manufacturing the prosthesis 10 includes the casting of the body 12 on a mandrel rod. The rod is dipped in a solution containing the polymer in order to coat the surface of the rod. The mandrel is withdrawn from the solution and the coating is cured to form a smooth outer surface. The prosthesis is removed from the mandrel and is then turned inside out so that the smooth air-cured surface 42 now forms the inner wall of the prosthesis. The very smooth polymer inner surface 42 of the prosthesis is highly non-thrombogenetic.

Figure 2:
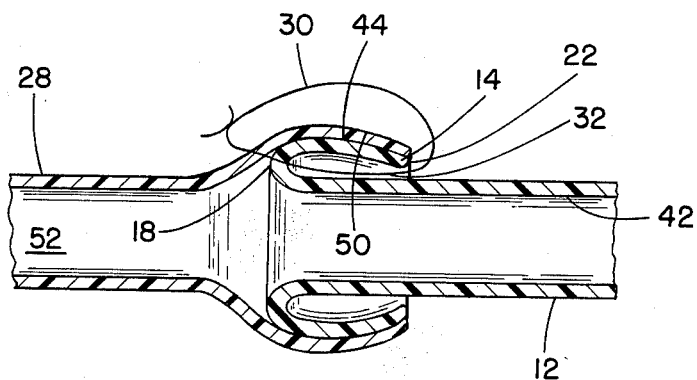
FIG. 2 is a cross-sectional view of the prosthesis showing the natural vessel overlapping the prosthesis.

The prosthesis cuffs 14 and 16 are formed by turning back the edges of the prosthesis on top of the body 12 to form the rounded ends 18 and 20. The outer surface 44 of the cuffs 14 and 16 is also formed of a smooth air-cured surface. As shown in FIG. 2, by folding back the ends to form the cuff 14, the endothelial surface 50 of the tubular organ 28 contacts the smooth polymer surface 44. Thus, the tubular organ 28 is attached to the prosthesis 10 away from the cut end 22 of the prosthesis 12, thereby minimizing infection and granulation tissue formation at the anastomosis site. Furthermore, when used as a vascular prosthesis, the area of anastomosis is separated from the blood passing through the vessel thereby minimizing thrombosis and neointimal hyperplasia. Therefore, the prosthesis of the present invention is well-suited for the repair of small blood vessels of 6 mm. or less, preferably from between 4 mm. to 6 mm., since occlusion of the prosthesis will not occur.

The mandrel rod used in the manufacturing process is preferably a highly polished glass rod that is first cleaned in quarterinary soap and acetone. However, other smooth nonporous materials are suitable for this mandrel rod, such as, Teflon or stainless steel. The rod is placed in a holder on a motorized drive unit which slowly lowers the rod into the polymer solution. The drive unit then reverses and pulls the prosthesis mandrel out. The speed of this dipping process is critical in that dipping too fast will carry air along and form bubbles, and withdrawal too fast will pull up too much polymer causing runs and sags. Preferably, the drive unit should lower and raise the mandrel at the rate of approximately 10 cm/min. Repeat dipping is used to increase the prosthesis wall thickness. The wall thickness of the vessel prosthesis can also be controlled by varying the concentration of the polymer. Generally, concentrations between 10 and 20% of solid polymer are appropriate depending upon the wall thickness compliance desired. One to two hours are allowed between coats to permit drying. The solvent dissolved segmented polyether polyurethane polymers are unique in that there is no onion-skinning produced by repeated coats. The polymer dries essentially from the inside out with each layer dissolving into the preceding layer so that the vascular prosthesis wall is formed into one solid unit. Wall thicknesses of approximately 0.05–0.15 mm. have been shown in bench studies to have essentially the identical compliance as a natural vessel. Generally, two or three coats are used for forming the prosthesis body and an additional coat is placed only on the ends to give added strength to the cuffs.

Alternatively, the prosthesis 10 may be coated with the Polymer by the cold-drawing coextrusion technique disclosed in U.S. Pat. No. 4,497,849, issued to Hughes et al., Hughes being a common co-inventor with the present application. The mandrel is held stationary in an extruding jig and coating reservoirs are pulled up on the mandrel to coat the mandrel with the polymer.

After the appropriate number of coats have been applied, either by the dipping or coextrusion process, the finished prosthesis is air-cured at 50°–60° C. for 24 hours. Air curing allows for a greater concentration of the soft segment polyether molecules to form a smooth outer surface on the prosthesis. The coated rod is then placed in distilled water for 24 hours to remove any residual solvents from the polymer segments. In addition, the hydrated prosthesis has a very low coefficient of friction facilitating the removal of the prosthesis from the rod. Furthermore, the hydrated prosthesis will initially present a lubricious surface to the blood and platelets which will lessen the chances for acute deposition while the body is hydrating the prosthesis.

Figure 3:
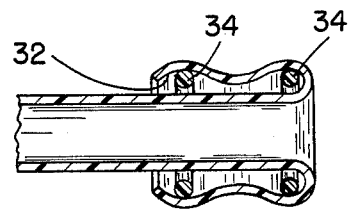
FIG. 3 is cross-sectional view of another embodiment of the invention having ligation rings.
Figure 4:
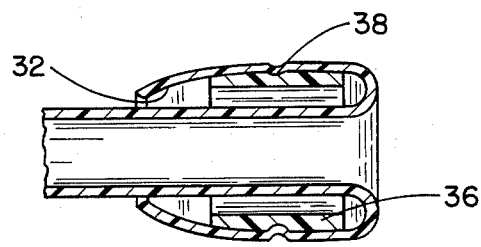
FIG. 4 is a cross-sectional view of another embodiment of the invention showing ligation bands.

The glass rod is then removed and the prosthesis is turned inside out so that the less thrombogenetic air cured surface will be the blood contact surface. The prosthesis can now be trimmed to the desired length. The ends of the prosthesis 10 are now turned back on themselves to form the prosthesis cuffs 14 and 16. At this time, the rings 34 or the bands 36 may be inserted as shown in FIGS. 3 and 4.

In order to fix the cuffs 14 and 16 in position, the entire prosthesis is again placed on a mandrel and heat set at 270° F. for 45 minutes at 15 psi. The heat setting permits altering the shape of the vascular prosthesis without adversely affecting the polymer structure. Thus, specifically curved sections can be made that allow the prosthesis to be bent around obstacles. Once the heat setting is completed the ends of cuffs 22 and 24 are welded to the tubular body 12 as shown in FIG. 1. The bonding is performed by placing four-six small drops of a 10% dilute polymer solution around the cuff ends at 60°-90° intervals. This spot bonding helps prevent the cuff ends from unrolling during the vascular anastomosis process. The prosthesis is now ready to be sutured within the vessel to be repaired.

The vascular prostheses of the present invention are highly compliant prostheses that can pulsate just like a normal vessel. The surface tension of the segmented polyether polyurethane is within the range of 20-30 dynes per cm. This surface tension permits minimal platelet adherence and low thrombogenicity. The prosthesis has an ultimate stress failure of approximately 6,000 psi with an elongation factor of 750%. The highly compliant prosthesis of the present invention will reduce failures and improve downstream tissue perfusion. In addition, this compliance may allow the continuation of laminar flow from the vessel through the prosthesis.

In FIG. 2, there is shown in representative form, how the prosthesis cuff 14 is sutured to the vessel or other tubular organ 28. The prosthesis 10 is anastomosed to the recipient vessel 28 by passing the sutures 30 through a cavity 32 between the cuff 14 on the body 12 through the fold end 18 of the cuff 14 and then into the vessel 28 on the endothelial surface 50. The cuffs 14 and 16 of the prosthesis are therefore within the lumen 52 of the vessel. This results in the endothelial surface 50 being exposed to the air-cured, smooth, non-thrombogenetic polymer surface 42 and the rounded ends 18 of the prosthesis 10 rather than the potentially irritating sharp ends of a cut graft or prosthesis. In addition, because the sutures 30 exit from the turned end of the prosthesis cuffs 14 and 16 and immediately penetrate the vessel 28, almost no sutures 30 are exposed to the blood contacting surface within the lumen 52. Sutures placed through a graft or prosthesis into the lumen of a vessel have the potential to create turbulence, to restrict flow and induce thrombosis. The prosthesis of the present invention avoids these problems.

Figure 5:
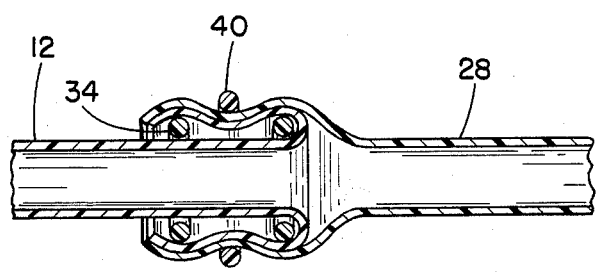
FIG. 5 is a cross-sectional view of the embodiment shown in FIG. 3 showing the prosthesis inserted within the vessel.

FIGS. 3 and 4 show alternative quick connect ligation means. In FIG. 3 there is shown a pair of ligation rings 34 embedded within the cavity 32. FIG. 4 shows a metal band 36 embedded within the cavity 32 having one or more of grooves 38. In these embodiments the prosthesis 10 is inserted within the tubular organ and they are tied together using a purse string type tie 40 that is tightened in the area between the ligation rings 30 as shown in FIG. 5, or within the grooves 38 of the metal band 36. The rigid rings 34 and the band 36 may be made of biocompatible materials such as stainless steel, platinum, titanium, nickel-cobolt metals or other similar biocompatible materials. In ligation, as illustrated in FIG. 5, the sutures will not be in contact with the blood contacting surface of the vessel thereby discouraging thrombosis.

Figure 7:
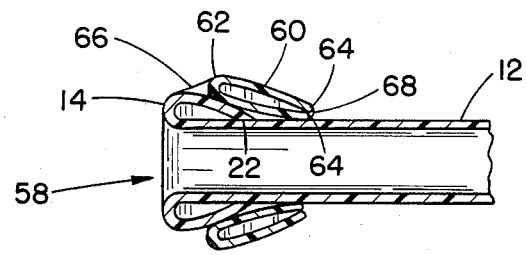
FIG. 7 is a cross-sectional view of the embodiment shown in FIG. 6.
Figure 6:
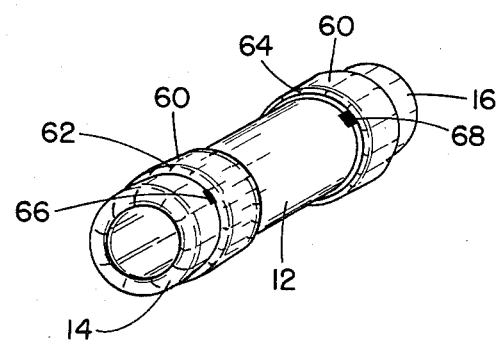
FIG. 6 is a prospective view of one end of the double-cuffed prosthesis of the present invention.
Figure 8:
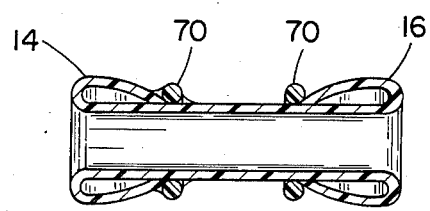
FIG. 8 is a cross-sectional view of another embodiment of the invention showing a polymer suture ring.

In another embodiment of the present invention shown in FIGS. 6 and 7, the prosthesis 58 includes a suture cuff 60 lying adjacent to each of the prosthesis cuffs 14 and 16. The suture cuffs 60 have a rounded end 62 that is bonded to the prosthesis cuff 14 by bonds 66 and cut ends 64, that are bonded to the tubular body 12 by bonds 68. An alternative to suture cuffs 60 is shown in FIG. 8 wherein a soft polymer ring 70 is placed around the tubular body 12 at the ends of the prosthesis cuffs 14 and 16.

The double cuffed prosthesis 58 is formed by first dipping a glass rod in the polymer solution, air curing and inverting as previously described. The prosthesis 58 is then placed back on the glass rod and the ends are folded back and circumferentially bonded in place. A suture cuff sleeve is made according to the same process by dipping a glass rod in the polymer solution and air curing the sleeve. The sleeve is removed from the rod and slid over the cuff ends of the prosthesis. As shown in FIG. 7, one end 64 of the suture cuff 60 is circumferentially bonded to the prosthesis. The sleeve is then folded back over itself so that both ends 64 are adjacent to each other to form the double layered suture cuff 60. The suture cuff 60 circumferentially surrounds the tubular body 12 with the rounded or fold end 62 overlapping the free end of the prosthesis cuff 14. This entire assembly is now heat set at 270° F. for 45 minutes. After cooling, the junction between the back end 22 of the prosthesis cuff and the rounded end 62 of the suture cuff 60 are held together with the diluted polymer bonds. The prosthesis 58 is then removed from the rod and soaked in water for 24 hours.

Figure 9:
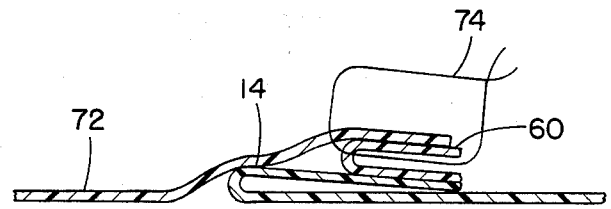
FIG. 9 is a cross-sectional view of the embodiment of FIG. 7 showing the prosthesis inserted within the vessel.

When suturing the double cuff prosthesis 58 to a host vessel or other tubular organ 72, the sutures 74 are first passed under and through the suture cuff 60 and then into the cut end of the recipient vessel 72 as shown in FIG. 9. This results in the host vessel 72 being pulled up and over the prosthesis cuff 14 and fixed to the suture cuff 60. By placing the suture cuff 60 away from the ends of the prosthesis 58, the suturing material is away from the blood contact surface which aids in reducing turbulence, tissue reactivity, and thrombosis.

Figure 10:
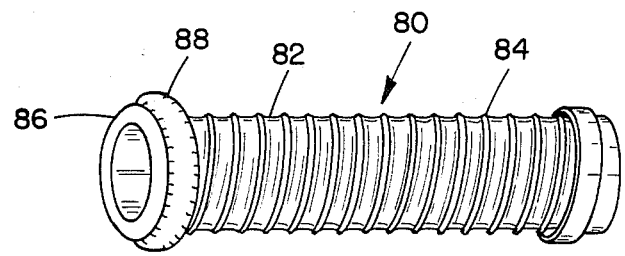
FIG. 10 is a prospective view of a trachea prosthesis.
Figure 11:
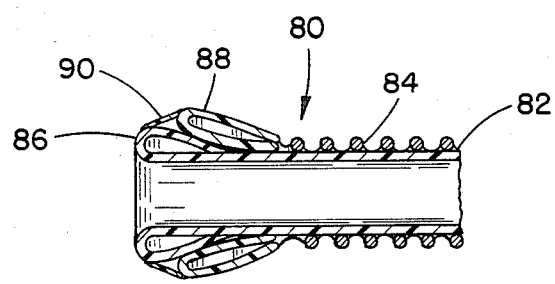
FIG. 11 is a cross-sectional view of the prosthesis of FIG. 10.

In a further embodiment, the tubular prosthesis of the present invention is adapted for use as a prosthetic trachea. FIG. 10 shows a prospective view of a trachea prosthesis. The prosthesis 80 includes a main tubular body 82 formed in accordance with the processes previously described, that has been spirally wrapped with support coils 84. The prosthesis 80 includes the turned back ends forming the prosthesis cuffs 86 and the additional suture cuffs 88 which are both bonded to the tubular body as described above. As can be more readily seen in the cross-sectional view in FIG. 11, the support coils 84 are all bonded to the tubular body 82 with the polymer bonding solution. The support coils may be made of nickel cobalt alloy, known as MP-35 spring wire that is precoated with a polymer, preferably segmented polyurethane. Any of the previously described coating techniques may be used to coat the coils. Once the coils have been spirally wrapped around the tubular body, the entire prosthesis is given an additional coat of polymer to bond the coils to the body.

The embodiment shown in FIG. 10 is a straight prosthesis for tracheal replacement in the cervical and upper thoracic regions. The prosthesis is sutured to the live trachea using the suture cuffs 88 similar to that shown in FIG. 9. If the suture cuffs are not provided, anastomosis can be performed with the prosthesis cuffs 86 as shown in FIG. 2. On those prostheses where it is desirable to encourage the ingrowth of fibrous tissue at the anastomosis, either dacron or graphite fibers 90 are wrapped circumferentially around the prosthesis between the rolled back prosthesis cuff 86 and the suture cuff 88.

Fibers 90 are bonded to the body of the graft with a polymer.

Figure 12:
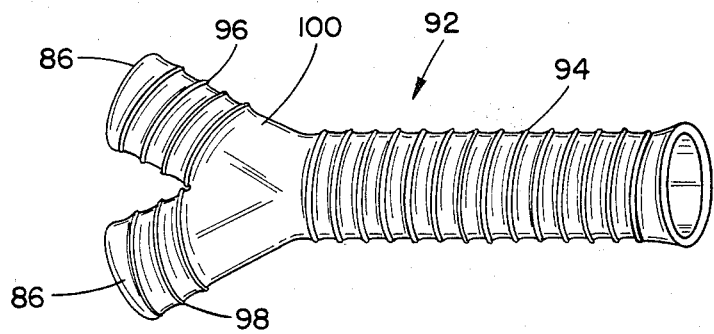
FIG. 12 is a prospective view of a Y sectioned trachea prosthesis.

FIG. 12 shows a Y shaped tracheal prosthesis suited for the replacement of the thoracic trachea and the two main bronchi. The Y shaped prosthesis 92 is formed by fabricating three separate straight sections 94, 96 and 98 and joining the sections together at section 100 by a polymer solvent bond. The anastomotic connection for the trachea is the same as that for the straight prosthesis. The bronchial connectors are preferably of a quick connect ligation ring design that are molded into prosthesis cuffs 86 of the Y prosthesis in sections 96 and 98. The ligation rings may be fabricated identical to the rings and metal bands shown in FIGS. 3 and 4. The ligation rings are used in the bronchi to minimize suturing the bronchi and thus lessening the chance for a leakage postoperatively. A third type of tracheal prosthesis is adapted to connect the trachea with one main bronchial branch. The third type includes a straight section 94 and one of the Y branches 96 or 98, which would be useful in conjunction with total removal of the lung on the opposite side.

The tracheal prostheses of the present invention are air tight, are made from material indifferent to body fluids and provide a sufficient degree of flexibility in all axes to maintain an open airway. The unique method of forming the tubular body provides a highly polished, wettable, relatively slippery lumen so that secretions from the distal respiratory tree are effectively removed despite the absence of associated epithelium.

While illustrative embodiments of the subject invention have been described and illustrated, it is obvious that various changes and modifications can be made therein without departing from the spirit of the present invention which should be limited only by the scope of the appended claims.

What is claimed is:

1. A cuffed tubular organic prosthesis for repairing or replacing tubular organs comprising:
    a flexible tubular body having an inside diameter substantially equal to the inside diameter of an organ to be repaired or replaced; and
    a prosthesis cuff on each distal end of said tubular body integral with said tubular body distal ends, each of said prosthesis cuffs having a rounded end for insertion within an open end of the organ and a free end bonded to said tubular body thereby forming a continuous smooth surface extending from the inner surface of the tubular body to the outer surface of the cuff, each of said prosthesis cuffs being adapted to be secured to the end of the tubular organ overlapping each distal end of said tubular body;
    said tubular body and each of said prosthesis cuffs together forming a unitary, non-resorbable member adapted to extend permanently between open ends of a tubular organ.

2. The cuffed tubular organic prosthesis of claim 1 further including a pair of rigid rings embedded between each of said prosthesis cuffs and said tubular body.

3. The cuffed tubular organic prosthesis of claim 1 further including a pair of metal bands having a plurality of grooves, one each of said metal bands being embedded between each of said prosthesis cuffs and said tubular body.

4. The cuffed tubular organic prosthesis of claim 2 wherein said rigid rings are made of a biocompatible material.

5. The cuffed tubular organic prosthesis of claim 3 wherein said bands are made of a biocompatible material.

6. The cuffed tubular organic prosthesis of claim 4 wherein said biocompatible material is selected from the group consisting of platinum, titanium, nickel cobolt metal and stainless steel.

7. The cuffed tubular organic prosthesis of claim 5 wherein said biocompatible material is selected from the group consisting of platinum, titanium, a nickel cobolt metal and stainless steel.

8. The cuffed tubular organic prosthesis of claim 1 further including a suture cuff lying adjacent to each prosthesis cuff, each of said suture cuffs having a rounded end and a pair of cut ends, each rounded end of said suture cuffs facing the rounded end of the respective adjacent prosthesis cuff.

9. The cuffed tubular organic prosthesis of claim 8 wherein said suture cuffs circumferentially surround said tubular body and overlap the free end of said prosthesis cuffs.

10. The cuffed tubular organic prosthesis of claim 8 wherein said suture cuffs have two layers formed by folding one end of a sleeve adjacent to the other end of said sleeve.

11. The cuffed tubular organic prosthesis of claim 8 wherein said rounded end of each of said suture cuffs is bonded to the respective adjacent prosthesis cuff and wherein said cut ends of said suture cuffs are bonded to said tubular body.

12. The cuffed tubular organic prosthesis of claim 1 further including a soft polymer ring around said tubular body at the free end of said prosthesis cuff.

13. A cuffed tubular organic prosthesis for repairing or replacing tubular organs comprising:
    a flexible tubular body having a smooth air cured inner surface formed by coating a mandrel with a polymer solution, air curing said coating to form a smooth outer surface, removing the mandrel and turning said tubular body inside out so that said air cured smooth surface forms the inner wall of said tubular body, said tubular body having an inside diameter substantially equal to the inside diameter of an organ to be repaired or replaced; and
    a prosthesis cuff on each distal end of said tubular body, each of said prosthesis cuffs having a continuous smooth air-cured surface extending from the inner surface of the tubular body to the outer surface of the cuff, said cuffs being formed by folding the edges of said tubular body back over said tubular body forming a rounded end for insertion within an open end of said organ and bonding said edges to said tubular body, each of said prosthesis cuffs being adapted to be secured to the end of the tubular organ overlapping each distal end of said tubular body;
    said tubular body and each of said prosthesis cuffs together forming unitary, non-resorbable member adapted to extend perminantly between open ends of a tubular organ.

14. The cuffed tubular organic prosthesis of claim 1 or 8 or 13 wherein the tubular body is made of a segmented polyether polyurethane.

15. The double cuffed tubular organic prosthesis of claim 13 wherein said flexible tubular body has an inside diameter or 6 mm or less.

16. The cuffed tubular organic prosthesis of claim 1 further including support coils spirally wrapped around said flexible tubular body.

17. The cuffed tubular organic prosthesis of claim 8 further including support coils spirally wrapped around said flexible tubular body.

18. The cuffed tubular organic prosthesis of claim 16 further including a double layered suture cuff surrounding said tubular body and overlapping the free end of one of said prosthesis cuffs, and ligation means imbedded between the other of said prosthesis cuffs and said tubular body.

19. The cuffed tubular organic prosthesis of claim 16 wherein said tubular body is in the shape of a Y having first and second bifurcated sections and a main section.

20. The cuffed tubular organic prosthesis of claim 19 further including a double layered suture cuff surrounding the prosthesis cuff on the main section and ligation means imbedded within the prosthesis cuffs on each of the bifurcated sections.

21. The cuffed tubular organic prosthesis of claim 16 wherein said flexible tubular body includes a main section and a tapered section.

22. The cuffed tubular organic prosthesis of claim 21 further including a double layered suture cuff surrounding the prosthesis cuff of said main section, and ligation means imbedded within the prosthesis cuff of said tapered section.

23. The cuffed tubular organic prosthesis of claim 16 or 17 wherein said coils are made of wire coated with segmented polyether polyeurythane.

24. The cuffed tubular organic prosthesis of claim 16 or 17 or 18 or 20 further including a fiber sleeve wrapped circumferentially around the distal ends of said prosthesis.

25. The cuffed tubular organic prosthesis of claim 24 wherein said fibers are dacron or graphite.

26. The cuffed tubular organic prosthesis of claim 25 wherein said fabric is bonded to said tubular prosthesis.

* * * * *